United States Patent [19]

Stevens

[11] Patent Number: 4,630,326
[45] Date of Patent: Dec. 23, 1986

[54] MICRO-STROKE MECHANICAL TOOTHBRUSH

[76] Inventor: Robert B. Stevens, P.O. Box 26284, Honolulu, Hi. 96825

[21] Appl. No.: 755,157

[22] Filed: Jul. 15, 1985

[51] Int. Cl.$^4$ .............................................. A46B 13/06
[52] U.S. Cl. .................................................. 15/22 R
[58] Field of Search ........................... 15/22 R, 22 A; 128/62 A, 66; 433/131

[56] References Cited

U.S. PATENT DOCUMENTS

| | | | |
|---|---|---|---|
| 3,214,775 | 11/1965 | Murov et al. ........................ | 15/22 R |
| 3,484,885 | 12/1965 | Deines et al. ....................... | 15/22 R |
| 3,524,208 | 8/1970 | Mattingly ............................ | 15/22 R |
| 4,534,340 | 8/1985 | Kerr et al. ...................... | 15/22 R X |
| 4,542,552 | 9/1985 | d'Argembeau .................. | 15/167 R |

FOREIGN PATENT DOCUMENTS 3143196  5/1983  Fed. Rep. of Germany ..... 15/22 R

Primary Examiner—Edward L. Roberts

[57] ABSTRACT

This mechanical toothbrush produces a micro-stroke 'shimmy' motion to a narrow-row soft bristle brush member. The handle part acts as a housing that holds the toothbrush stem and has two internal chambers; one of which holds a spring, the other inducts water into the hollow tubular stem of the toothbrush wherein said water will pass through to and wet the bristle brush member. The housing at the toothbrush stem end is contoured to prevent rotational motion of the toothbrush stem. The other end of the housing has a detatchable coupling to connect with a pulsed water driving source.

1 Claim, 6 Drawing Figures

MICRO-STROKE MECHANICAL TOOTHBRUSH

BACKGROUND OF THE INVENTION

1. Field of Invention

This toothbrush is specifically designed to automatically deliver the medically recommended plaque removal brushing technique which is manually impossible to duplicate.

2. Description of the Prior Art

Oral hygiene has improved over the years largely due to continuous improvements in our knowledge of dental care and the technology related to these improvements.

Toothbrushes come in a variety of designs. Electric type toothbrushes, of which this invention is closely related, fall into U.S. Patent class 15 subclass 22. A recently patented and technically sophisticated electric toothbrush has a U.S. Pat. No. 4,365,376 to Oda et al which was assigned to Matsushita Electric Works, Ltd. of Osaka, Japan. This device has both a toothbrush, with a reciprocal turning motion that is medically not recommended, and a nozzle member like that of the 'Water Pic' oral hygiene appliances manufactured by Teledyne Industries, Inc. of Fort Collins, Colorado. U.S. Pat. Nos. 4,302,186; 4,108,167; and Re. 27,274 were all assigned to Teledyne Industries, Inc. and pertain to their 'Water Pic' oral hygiene appliances.

No electric or mechanical toothbrush has even been manufactured or patented that accomplishes the specific motion, action, operation or purpose of this invention. Most electric toothbrush patents relate to the electrical or mechanical mechanisms used to power or hold the toothbrush. U.S. Pat. No. 4,458,374 to Hukuba in July of 1984 and U.S. Pat. No. 3,316,576 to Urbush, which was assignd to Scovill Manufacturing Co. of Connecticut, are two examples.

A toothbrush with an action in the same plane or direction of motion as my invention received U.S. Pat. No. 3,142,852 to E. A. Phaneuf and H. Springer, which was assigned to and manufactured by the General Electric Company. However, the stroke length of their toothbrush is much greater than the micro-stroke of my mechanical toothbrush; enough to cause a scrubbing action when placed on tooth surfaces. Also, the purpose and use of their toothbrush was to clean the entire tooth, including the biting surfaces, with a more vigorous action utilizing a conventional size and shape brush head. My invention uses a narrow-row soft bristle brush intended for use specifically on the sulcus which is at the interface of the tooth and gum. My invention is designed specifically for removing plaque at the sulcus. It is not a generalized toothbrush for cleaning the entire mouth. My invention has a specific micro-stroke motion that generates a 'shimmy' as opposed to a brushing or scrubbing action.

3. Disclosure Statement

I do not know of any mechanical toothbrush that uses a narrow-row soft bristle brush intended to specifically clean the sulcus of the teeth by means of a micro-stroke movement that occurs in one line of motion, in-line with the direction of the toothbrush stem and bristles; wherein when the tips of the bristles are placed into contact with teeth, gums or sulcus they remain where placed and produce only an agitation or 'shimmy' motion. I do not know of any mechanical toothbrush that uses a pulsating water stream to power the toothbrush. I do not know of any mechanical toothbrush that automatically wets the brush member so as to lubricate, rinse and cleanse. My invention has all of these features.

SUMMARY OF THE INVENTION

The primary object of the invention is to remove plaque from the sulcus of the tooth and gum without contributing to periodontal disease. This is accomplished primarily by the following three technical features. Feature one is a narrow row soft bristle brush member having a width of not more than about 0.2 inches. Feature two, is a specific motion called a micro-stroke which is a predetermined short stroke motion such that when the toothbrush is positioned into contact with the tooth, gum or sulcus the tips of the bristles tend to remain where placed; with only a slight agitation or 'shimmy' occurring at the tips of the bristles. Feature three, is directing the micro-stroke in one specific line of motion, in-line with the direction of the toothbrush stem and bristles.

A further object of the invention is to utilize a pulsating water flow to power the mechanical toothbrush.

A still further object of the invention is to provide a water discharge at the brush member thus helping to keep the brush wet and aid in the cleaning or rinsing of the teeth, gums and sulcus.

BRIEF DESCRIPTION OF THE DRAWING

In order that the invention may be more readily understood, reference will now be made to the accompanying drawings which show one embodiment thereof by way of example and in which.

DESCRIPTION OF THE PREFERRED EMBODIMENT

Figure 1:
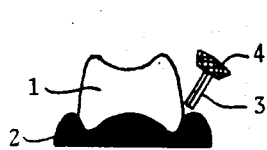
FIG. 1 is a top elevation view depicting proper placement of the toothbrush bristle member for cleaning the sulcus.

Before explaining the present invention in detail it is to be understood that the invention is not limited in its application to the details of construction and arrangements of parts illustrated in the accompanying drawing, since the invention is capable of other embodiments and of bring practiced or carried out in various ways. Also, it is to be understood that the phraseology or terminology employed herein is for the purpose of description and not of limitation.

Referring now to the drawings wherein like reference numerals refer to like and corresponding parts throughtout the several veiws, the preferred embodiment of the invention is disclosed in FIGS. 1-6 inclusive.

Referring first to FIG. 1, this drawing illustrates the proper positioning of the narrow-row soft bristle brush member 3 of the micro-stroke mechanical toothbrush. The micro-stroke 'shimmy' motion of the tips of the bristles agitates and helps remove plaque and bacteria from the sulcus of the teeth; the sulcus being at the interface between the tooth 1 and gum 2. The microstroke motion is in one line of direction, in-line with the length of the toothbrush stem 4. The micro-stroke 'shimmy' is of such a short length that the bristle tips when placed in contact with the tooth, gum or sulcus temd to remain where placed with only a slight agitation occurring at the tips of the bristles.

The mechanical toothbrush of this embodiment is powered by a pulsating water source wherein the pulsating water flow is conducted to the mechanical toothbrush through a flexible hollow tubing 16. A female detachable coupling piece 15 attached to the male detachable coupling piece 14 of the mechanical toothbrush. This toothbrush consists of only 3 individual parts which will now be discussed in detail.

The toothbrush stem 4 has a hollow channel 5 which runs from the water induction ports 11, where water enters the hollow channel 5, through the toothbrush stem 4 where water discharges onto the narrow-row soft bristle brush member 3. The wet brush helps to lubricate the bristles and rinse the sulcus of bacteria and plaque.

Figure 2:
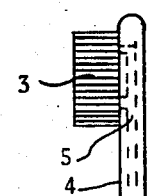
FIG. 2 is a side elevation view of the toothbrush.
Figure 3:
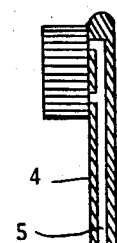
FIG. 3 is a side cross-sectional view of the toothbrush.

As a pulse of water enters the mechanical toothbrush it enters the pressurizing conduit 13 where it applies pressure or force upon the base of the toothbrush stem 12 causing the toothbrush stem to move upward in the direction of the flow. When the base of the toothbrush stem reaches the depressurizing chamber 10, water enters the depressurizing chamber and enters the water induction ports of the toothbrush stem. Spring 8 acts upon the toothbrush flange 9 which pushes the flange downward so the flange and the base of the toothbrush stem return to the fully lowered at-rest position; in anticipation of the next pulse of water. The spring 8 and flange 9 limit the movement of the toothbrush stem 4 so that the toothbrush makes only a predetermined microstroke 'shimmy'. FIGS. 2 and 3 illustrate the position of the toothbrush stem at about one third of its vertical or upward movement range. The toothbrush having 6 holds the spring and flange assembly in spring chamber 7.

Figure 4:
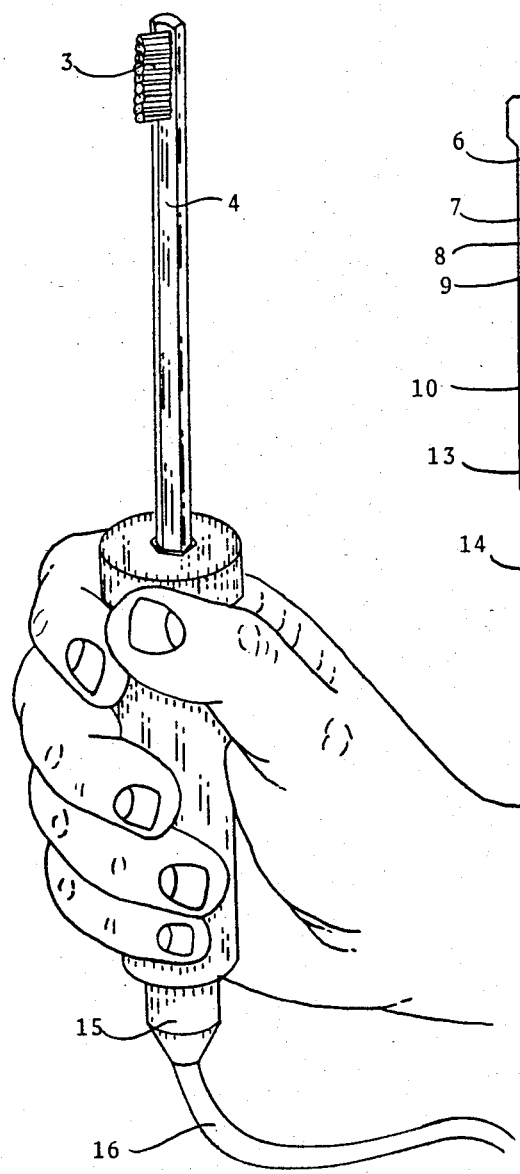
FIG. 4 is a perspective view of the toothbrush shown rotated 45° counter-clockwise from that of FIG. 2 or FIG. 3, and held in a childs hand, and supplied with a pulsating water source.
Figure 5:
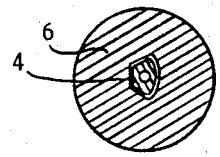
FIG. 5 is a cross-sectional view taken along line 5—5 of FIG. 3.
Figure 6:
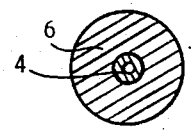
FIG. 6 is a cross-sectional view taken along the line 6—6 of FIG. 3.

The cross-sectional views 5—5 and 6—6 in FIG. 3 illustrate the changing shape of the toothbrush stem. In FIG. 6 the round shape improves the seal between the toothbrush stem 4 and the toothbrush housing 6, and reduces the surface area for friction. FIG. 5 shows the partial hexagon shape of the toothbrush stem 4 which prohibits rotational movements of toothbrush. FIG. 4 illustrates the mechanical toothbrush in a childs hand.

Successful use of the micro-stroke mechanical toothbrush simply involves drifting the toothbrush angled in the proper position as shown in FIG. 1. The user may wish to add an occasional sweep from the sulcus along the side of the tooth in the direction of the distal 'biting' tooth surface. This toothbrush provides a specific action, called a micro-stroke, that cannot be accomplished by the human hand. It is this specific motion that successfully and safely removes plaque and bacteria where they are of the greatest risk of causing periodontal disease. Adding human motion to this toothbrush, in the form of brushing or scrubbing, is therefore discouraged.

I claim as my invention:

1. A mechanical toothbrush for cleansing and rinsing the sides of the teeth and sulcus by means of a narrow-row soft bristle-brush member that moves through a short-stroke in the direction of the longitudinal axis of the toothbrush stem such that the tips of the bristles of the bristle-brush member tend to remain where placed and produce only an agitation, and wherein, an intermittent stream of water pressure pulses powers the toothbrush and is discharged at the bristle-brush member, comprising;

a tubular toothbrush stem with a hollow channel within the toothbrush stem that receives water through induction ports near the base of the toothbrush stem wherein said water travels within the hollow channel to a bristle-brush member, distal to the toothbrush stem water induction ports, wherein said water is discharged, and wherein, the cross-sectional area of the bristle-brush member has a narrow width of not more than about 0.3 cm by a length of any dimension wherein the length in cross-section is generally parallel in direction to that of the longitudinal axis of the toothbrush stem, and wherein, proximal to the bristle-brush member, within the toothbrush housing, the toothbrush stem is widened to form a flange, and wherein, the toothbrush stem is round in cross-section near its base, where it acts as a piston, and wherein, the toothbrush stem has several flat sides within the toothbrush housing, proximal to the bristle-brush member, so as to prevent rotational motion of the toothbrush stem;

a generally cylindrical housing, that acts as a handle for the toothbrush stem, the longitudinal axis of the housing being in the same direction as that of the longitudinal axis of the toothbrush stem that the housing holds, in part, within it, wherein, within the housing there is a pressurizing conduit that increases the pressure of the intermittent water pressure pulses prior to their impacting upon the toothbrush stem base, and wherein, there is a depressurizing chamber that relieves the pressure of the water pressure pulses after the toothbrush stem has moved a pre-determined short-stroke length distance from the pressurizing conduit wherein the water is directed into the water induction ports of the toothbrush stem by pressure gradient, and wherein, the housing has a spring chamber that houses a spring that acts upon a flange on the toothbrush stem thereby encouraging the toothbrush stem to a position so that the toothbrush stem base is closest to the pressurizing conduit, and wherein, the housing closely holds the toothbrush stem within it.

* * * * *